United States Patent [19]
Fouckhardt et al.

[11] Patent Number: 5,572,328
[45] Date of Patent: Nov. 5, 1996

[54] OPTICAL DETECTOR INCLUDING BRAGG WAVEGUIDE STRUCTURE

[75] Inventors: Henning Fouckhardt, Hanover; Thomas Delonge, Brunswick, both of Germany

[73] Assignee: Hewlett-Packard Company, Palo Alto, Calif.

[21] Appl. No.: 388,349

[22] Filed: Feb. 14, 1995

[30] Foreign Application Priority Data

Apr. 27, 1994 [DE] Germany .......................... 94106551.8

[51] Int. Cl.⁶ .......................... G01N 21/05; G01N 21/85
[52] U.S. Cl. .......................... 356/440; 356/410; 356/436; 385/12
[58] Field of Search .................... 356/410, 440, 356/436, 437; 385/12

[56] References Cited

U.S. PATENT DOCUMENTS 4,880,752 11/1989 Keck et al. .......................... 385/12 X
5,273,633 12/1993 Wang et al. .......................... 204/180.1

FOREIGN PATENT DOCUMENTS 1-97841 4/1989 Japan .................................... 356/440

OTHER PUBLICATIONS

EPO Search Report, EP 94 10 6551, Oct. 1994.
A Microfabricated Flow Chamber For Optical Measurements In Fluids, Sobek et al., Jul. 2, 1993, 219–224, proceedings of Micro Electro Mechanical Systems, Feb. 1993.

Database WPI, Section Ch., Week 9144, Derwent Publications Ltd., London, GB; Class J04, AN 91-322901 & SU-A-1 610 410 (Biolog Appts Res In) 30 Nov. 1990, abstract.

A Silicon Flow Cell For Optical Detection In Miniaturized Total Chemical Analysis Systems, Verpoorte et al., 8253b Sensors & Actuators, B Chemical Jan. 1992, pp. 66–70.

Low–Loss Antiresonant Reflecting Optical Waveguide On Si Substrate In Visible–Wavelength Region, Kokubun, Y., Electronics Letters, Aug. 14, 1986, vol. 22 No. 17, pp. 892–893.

Primary Examiner—Vincent P. McGraw

[57] ABSTRACT

An optical detector for use in liquid chromatography systems or capillary electrophoresis systems comprises an optically transparent detector body through which an analyte channel extends, a fluid containing the analyte being adapted to be guided through said analyte channel. In order to increase the detection sensitivity, the light path between a light source introducing light and an optoelectric sensor element of the liquid chromatography system or capillary electrophoresis system is constructed as a Bragg waveguide structure extending at least along a sublength of said analyte channel essentially in the channel direction.

9 Claims, 4 Drawing Sheets

OPTICAL DETECTOR INCLUDING BRAGG WAVEGUIDE STRUCTURE

FIELD OF THE INVENTION

The present invention deals with an optical detector device for an analytical measurement system, said optical detector device being particularly suitable for use in liquid chromatography systems or capillary electrophoresis systems.

In particular, the present invention deals with an optical detector device which is adapted to be used in chromatographs and in capillary electrophoresis devices and which has a high detection sensitivity.

TECHNOLOGICAL BACKGROUND

In analytical measurement procedures, fluid substances are analyzed among other substances. Two of the most common methods for the analysis of fluid substances are chromatography and capillary electrophoresis.

A chromatograph as well as a capillary electrophoresis device consist, in principle, of three units, viz. firstly the so called injector by means of which the substances containing the analyte, namely in most cases liquids, are injected into the system with a nanolitre or picolitre accuracy, secondly the separation column on which a spatial separation of the substances contained in the injected solution is carried out by means of physical or chemical interactions so that different substances will arrive at the end of the separation column at different times, and thirdly the detector at the exit of the separation column, said detector indicating the arrival of the individual substances contained in the solution.

The type of detection suitable for most classes of substances is the optical detection. When optical detection is carried out, light having a suitable wavelength is normally sent transversely through the separation column at the end of said separation column in an optical detector device and, consequently, it is sent through the solution to be analyzed. A certain percentage of the light is absorbed by the substances. The spectral position of the absorption peaks and their form make it possible to provide information on the nature and the concentration of the substances.

For various reasons, capillaries with inner diameters in the range of from a few micrometers up to approx. 100 micrometers are used as separation columns in the field of capillary electrophoresis and more and more also in the field of chromatography. When the light passes through the separation column transversely to the longitudinal direction thereof, the path of interaction between the light and the matter or rather the substance to be analyzed is very short so that the possible detection sensitivity is comparatively low.

In order to achieve a longer path of interaction between the light and the analyte-containing fluid in a fluid channel at the end of the separation column, it would be desirable to guide the light directly in the solution over a certain distance along the fluid channel in the separation column.

The aqueous solutions used most frequently as a solution have refractive indices of approx. n=1.33, whereas the typical capillary materials have refractive indices of at least n=1.47 in the case of quartz. Hence, the usual way of guiding the light by means of total internal reflection is impossible, since, for this purpose, the medium in which the light is to be guided must have a refractive index which is higher than that of the capillary material.

A solution used in connection with commercially available chromatography systems is the measure of increasing the path length of the light along which an interaction with the solution can take place by widening the capillary locally to a bubble through which the light is guided.

Another solution is to guide the light in the direction of the column within the fluid by total internal reflection at the boundary fluid/inner capillary wall. As has already been explained, the total internal reflection requires a chemical solution having a higher refractive index than the adjacent layer.

The technical publication A. Manz, D. J. Harrison, E. Verpoorte, H. M. Widmer: Planar chips technology for miniaturization of separation systems: a developing perspective in chemical monitoring. Advances in Chromatography 33(1993) 1–65 discloses the measure of guiding the light by means of the normal Fresnel reflections. This leads to significant losses, especially with small inner diameters of the capillaries and high wavelengths.

Another solution is to guide the light by total internal reflection in the wall of the separation column in order to increase the interaction in miniaturized separation systems. This method utilizes the absorption of the transversely attenuated field components in the solution to be analyzed. However, also this known system necessitates comparatively long interaction paths between the light and the solution to be analyzed, since only the weak evanescent waves of the light are absorbed.

To achieve total internal reflection, there are two methods which can be chosen: the first one is to use a chemical solution with a high refractive index, said refractive index being higher than that of the material of the capillary. This is achieved e.g. by the combinations of salt solutions with Teflon PFA or PFE coatings, as has been described in U.S. Pat. Nos. 4,009,382 as well as 3,954,341. The second one is the method of coating the inner wall of the capillary with a material having a low refractive index. In the first-mentioned case, there are two disadvantages: the aqueous salt solution is undesirable in many analytical measurements and the Teflon materials mentioned above are not sufficiently transparent at shorter UV wavelengths of the light used. When the second method which has been mentioned is used, the inner wall of the fused silica capillary has to be coated with a material having a low refractive index, this material being e.g. an amorphous fluoropolymere.

SUMMARY OF THE INVENTION

Taking this prior art as a basis, it is therefore the object of the present invention to further develop an optical detector device for analytical measurement systems of the type mentioned at the beginning in such a way that an improved detection sensitivity is achieved in spite of the fact that the detector device has a simple structure and is easy to produce.

This object is achieved by an optical detector device for analytical measurement systems, in particular for use in liquid chromatography systems or capillary electrophoresis systems, comprising an analyte channel through which a fluid containing the analyte can be guided, and a light path extending through said analyte channel into which light coming from a light source can be introduced and from which light can be coupled out and introduced in an optoelectric sensor element of the analytical measurement system, at least part of the light path being defined by a waveguide, which is constructed at least partially as a Bragg waveguide structure in such a way that the light is guided through the analyte channel essentially in the channel direction at least along a sublength of said analyte channel.

In accordance with an important aspect of the present invention, the Bragg waveguide structure is implemented as a combined Bragg and ARROW (antiresonant reflecting optical waveguide) waveguide structure.

In accordance with the present invention, at least part of the light path is defined by a waveguide, which is constructed at least partially as a Bragg waveguide structure in such a way that the light is guided through the analyte channel essentially in the channel direction at least along a sublength of said analyte channel. The Bragg waveguiding used by the subject matter of the present invention is a type of waveguiding used in optical communications engineering. The present invention provides for the first time the use of this type of waveguiding for the purpose of solving the problems of analytical measurement procedures which have been outlined hereinbefore. The principle of Bragg waveguiding is that the light to be guided is reflected at the boundaries of the layers which have alternately high and low refractive indices and which follow the actual waveguide core. The refractive index of these layers can be lower, equal to or higher than the refractive index of the core. In the optical detector device according to the present invention, the core of the Bragg waveguide is defined by the analyte channel, i.e. by the channel through which the fluid containing the analyte is guided.

In accordance with an important aspect of the present invention, the optical detector device is constructed such that two related waveguide mechanisms are combined. In a first plane, which extends through the analyte channel, waveguiding is realized as Bragg waveguiding by means of Bragg reflecting layers covering the upper side and the bottom side of the analyte channel as well as of the reference channels, whereas waveguiding in the plane which is perpendicular to this plane and which extends through the analyte channel is realized by ARROW waveguiding. ARROW waveguiding is effected by the analyte channel and the reference channels extending in essentially parallel spaced relationship with said analyte channel, the refractive index of the optically transparent detector body of the detector device being higher than the refractive index of the fluid in the analyte channel as well as in the reference channels so that the areas of the detector body which are located between the analyte channel and the reference channels positioned adjacent said analyte channel act as first ARROW reflectors, whereas the areas of the detector body which are respectively located between the reference channels act as second, third, etc. ARROW reflectors. To cut a long story short, the analyte channel and the reference channels as well as the areas of the detector body which are located between these channels define sequences of layers having alternately high and low refractive indices, whereby an antiresonant reflecting optical waveguide structure (ARROW) is defined.

ARROW waveguiding is a special type of Bragg waveguiding, where the reflector thickness obey certain formular given in part "Description of the preferred embodiments of the invention" of this application.

In a preferred embodiment of the optical detector device according to the invention, the waveguide is constructed as an antiresonant reflecting optical waveguide (ARROW).

In another preferred embodiment of the optical detector device according to the invention, the waveguide is defined by Bragg reflecting layers in a plane extending through the analyte channel, and the waveguide is defined by an antiresonant reflecting waveguide structure in an additional plane which is perpendicular to said first-mentioned plane and which also extends through said analyte channel.

In another preferred embodiment of the optical detector device according to the invention, the analyte channel extends through an optically transparent detector body, at least one reference channel extending on either side of the analyte channel in parallel, spaced relationship therewith so that the analyte channel and the reference channels define in said detector body an antiresonant reflecting optical waveguide structure (ARROW) which is effective in a first plane.

In another preferred embodiment of the optical detector device according to the invention, the channels called reference channels herein do not act as reference channels in the sense of analytical measurements, but as reflectors only. The refractive index of the substance within these channels has to be similar to that of the fluid in the analyte channel.

In another preferred embodiment of the optical detector device according to the invention, the analyte channel and the reference channels are each provided with Bragg reflecting layers on two opposed boundary layers, said Bragg reflecting layers defining a Bragg waveguide structure in a second plane which extends perpendicular to the first plane.

In another preferred embodiment of the optical detector device according to the invention, the detector body comprises a substrate member and a cover member, said analyte channel and said reference channels being etched into said substrate member and/or said cover member with an essentially rectangular cross-section.

In another preferred embodiment of the optical detector device according to the invention, Bragg waveguiding is employed in both vertical and horizontal dimension. The reflector layers could be deposited by evaporation or chemical vapor deposition techniques.

In another preferred embodiment of the optical detector device according to the invention, the detector body is cylinder symmetrical and Bragg waveguiding is employed. The reflector layers could be deposited by chemical vapor deposition techniques.

In another preferred embodiment of the optical detector device according to the invention, the size of the cross-sectional dimensions of the analyte channel and of the reference channels is between 1 micrometers and 100 micrometers, and is preferably some ten micrometers if the vacuum detector wavelengths of the optical detector device range between 100 and 1000 nm, preferably between 190 nm and 600 nm.

In accordance with yet another important aspect of the invention, the core of the optical waveguide is defined by the analyte channel.

In another preferred embodiment of the optical detector device according to the invention, the refractive index of the optically transparent detector body is higher than the refractive index of the fluid in the analyte channel and is also higher than the refractive index of the fluid in the reference channels so that areas of the detector body which are located between the analyte channel and the reference channels positioned adjacent said analyte channel act as first ARROW reflectors, whereas said reference channels positioned adjacent the analyte channel act as second ARROW reflectors, and areas which are located between the respective reference channels act as additional ARROW reflectors.

BRIEF DESCRIPTION OF THE DRAWINGS

In the following, preferred embodiments of the optical detector device according to the present invention will be explained in detail with reference to the drawing enclosed, in which.

DESCRIPTION OF THE PREFERRED EMBODIMENTS OF THE INVENTION

Figure 1:
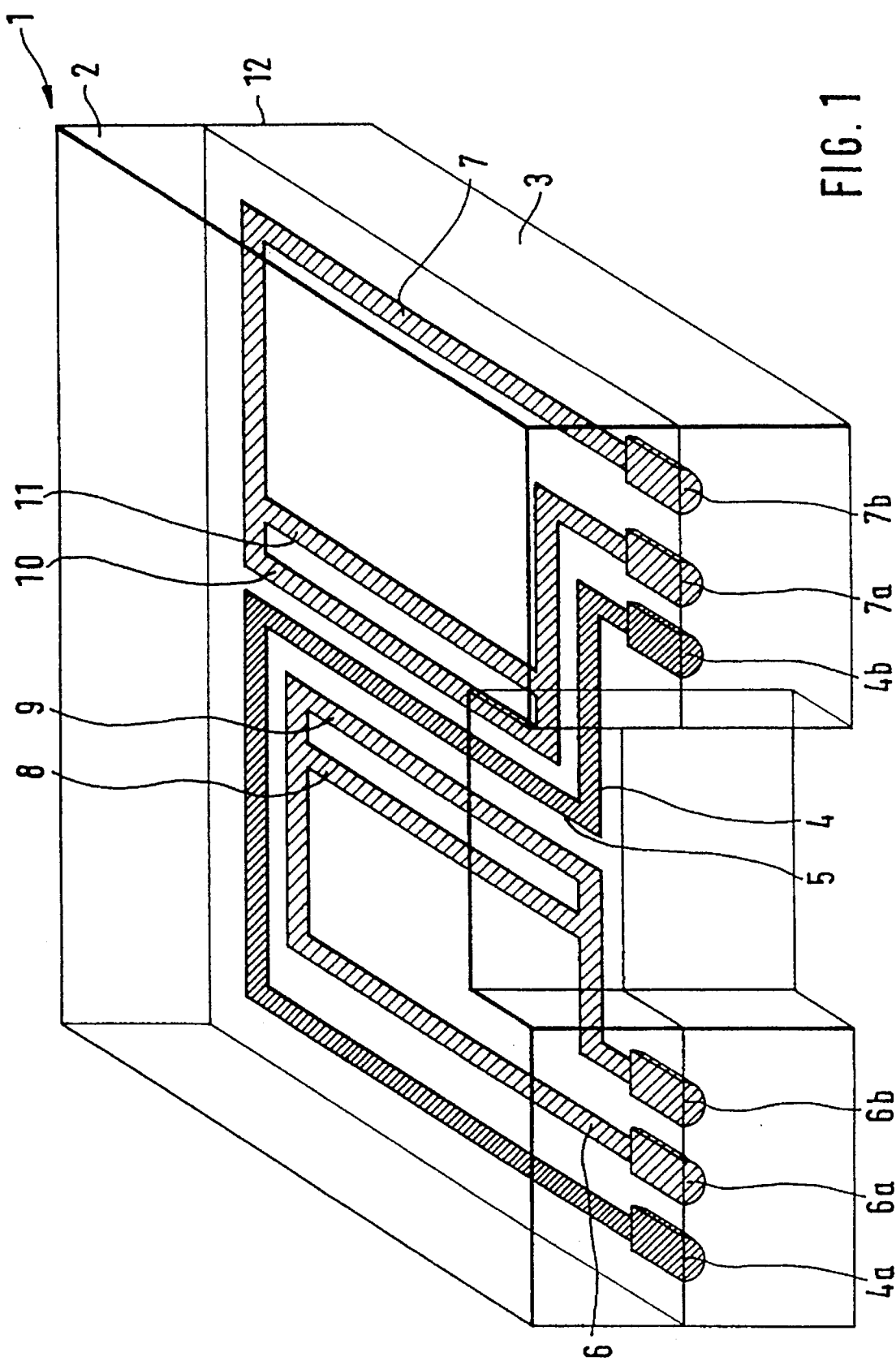
FIG. 1 shows a perspective view of an embodiment of the optical detector device according to the present invention.

As can be seen in FIG. 1, the optical detector device, designated generally by reference numeral 1, comprises essentially two parts, viz. a cover member 2 on the one hand and a substrate 3 on the other. The cover member 2 and the substrate 3 define, at the surfaces at which they face one another, an analyte channel 4 as well as reference channel sections 8, 9, 10, 11 of reference channels 6, 7 on both sides of a longitudinal section 5 of said analyte channel 4, said reference channel sections 8, 9, 10, 11 extending parallel to and in uniformly spaced relationship with said longitudinal section 5 of said analyte channel 4.

As will be explained in detail hereinbelow, a fluid is guided through the analyte channel 4, the analyte being contained or rather dissolved in said fluid. The reference channel sections 8, 9, 10, 11 are supplied with a fluid through the reference channels 6, 7, the refractive index of said fluid corresponding essentially to the refractive index of the fluid in the analyte channel 4.

In the area of an end face of the detector body 12 defined by the cover member 2 and the substrate 3, the two reference channels 6, 7 and the analyte channel 4 each end in capillary connectors 6a, 6b, 7a, 7b, 4a, 4b, which are adapted to be connected to suitable lines (not shown) used for supplying the reference fluid and the fluid containing the analyte.

The above-explained structure of the optical detector device 1 can be produced by standard processes in the field of semiconductor technology by means of which the channels 4, 6, 7 are defined in the cover member 2 and substrate 3, respectively, which consist of quartz, fused silica or of some other material, with the aid of photolithographic structuring of a resist, and are then excavated by wet-, plasma- or ion-etching.

Figure 2:
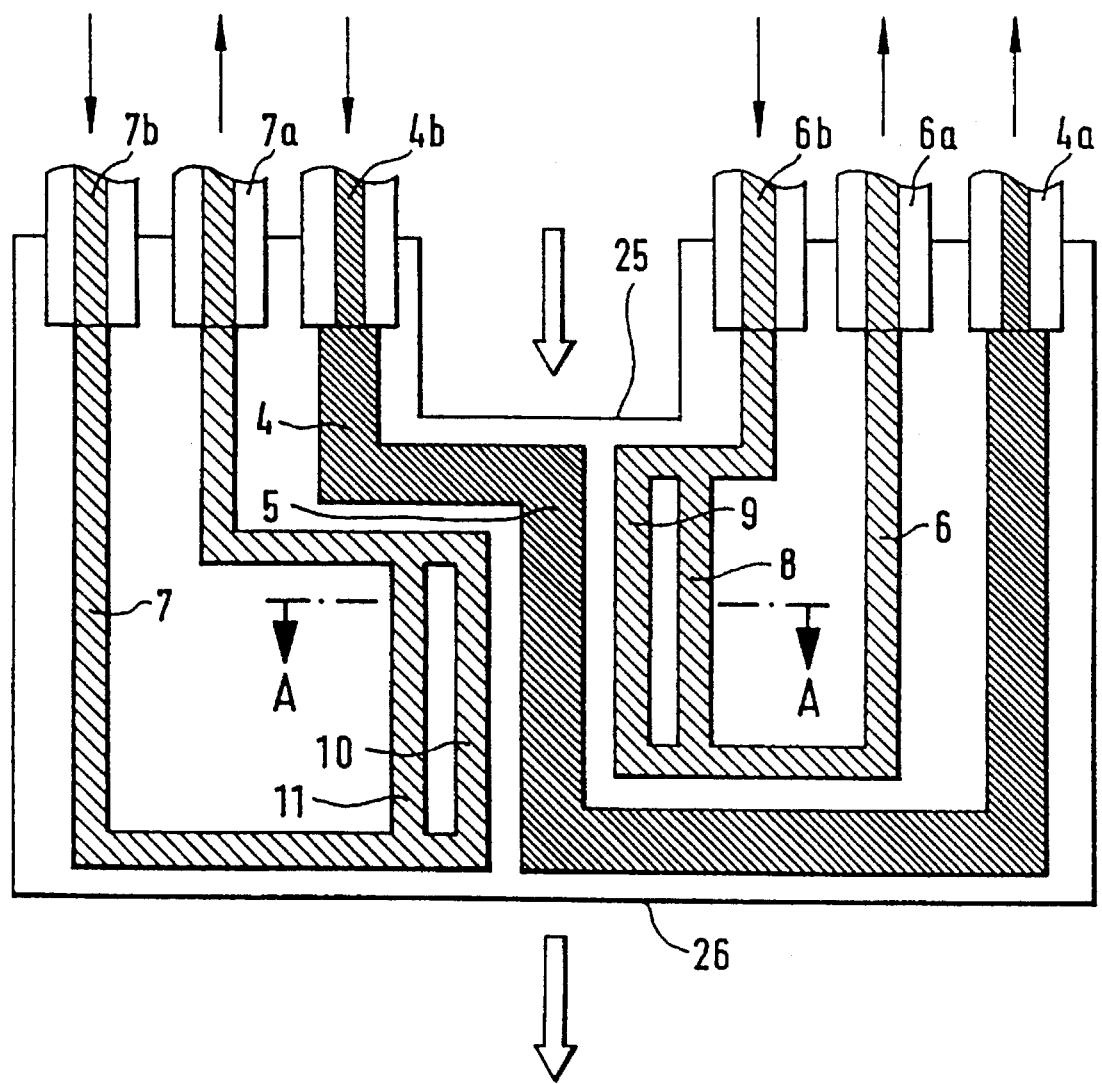
FIG. 2 shows a horizontal sectional view of the embodiment according to FIG. 1.
Figure 3:
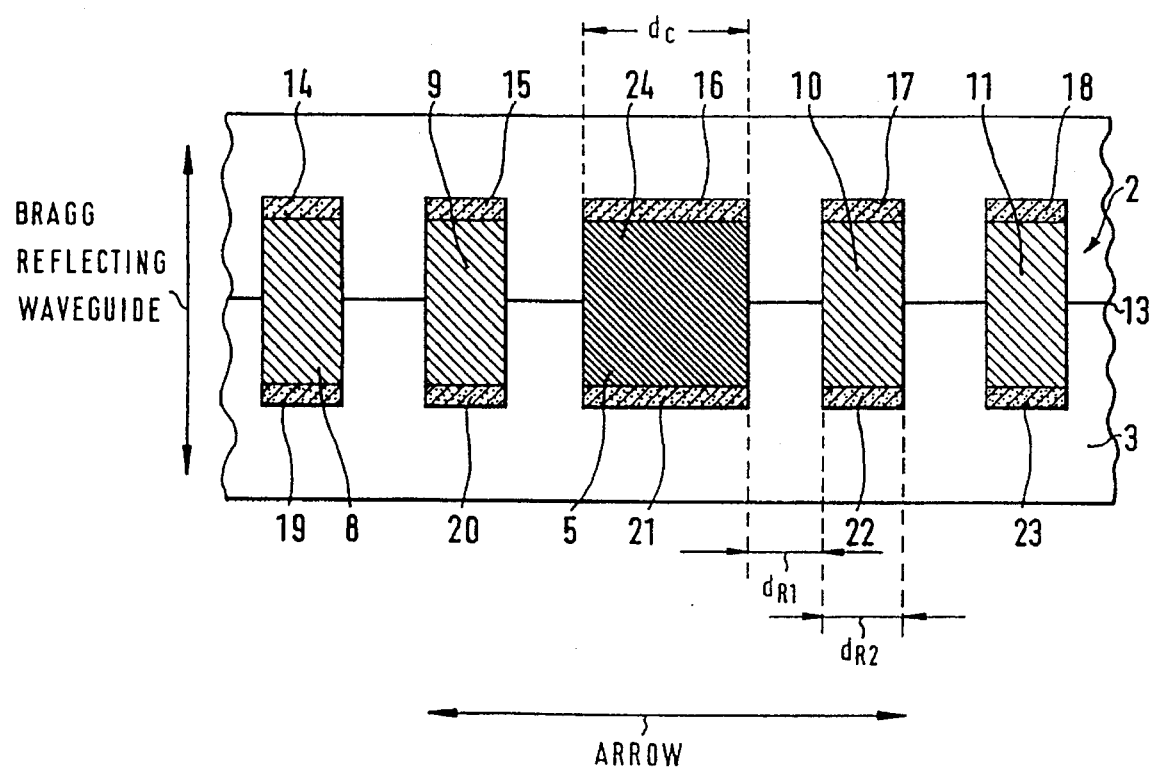
FIG. 3 shows a fragmentary vertical sectional view of the embodiment shown in FIG. 1 and 2, along the sectional line A—A.

As can be seen from FIG. 2 and the fragmentary cross-sectional view shown in FIG. 3, the respective base areas of the channels 4, 5, 6, 7, 8, 9, 10, 11, which have a substantially rectangular cross-section, are provided with Bragg reflecting layer structures 14, 15, 16, 17, 18 in the cover member 2 and 19, 20, 21, 22, 23 in the substrate 3, said Bragg reflecting layers extending parallel to the boundary 13 between said cover member 2 and said substrate 3.

In another embodiment, the channels 4, 5, 6, 7, 8, 9, 10, 11 are only in the substrate 3. The cover 2 is flat and coated with a continuous Bragg reflector structure, which combines Bragg reflecting layer structures 14, 15, 16, 17, 18 to one.

The above-described Bragg reflecting layers 14 to 23 can be deposited by evaporation or they can be produced by epitaxial growth in the case of the crystalline semiconductor materials.

Together with the respective areas of the detector body 12 lying between two reference channels 8, 9; 10, 11 or between one reference channel 9, 10 and the analyte channel 5, the reference channels 8, 9, 10, 11 form on either side of the core 24 four ARROW reflectors, the detector body area lying between the longitudinal section 5 of the analyte channel 4 and the neighbouring reference channel section 10 defining the first ARROW reflector, which has a higher refractive index than the core 24, whereas the neighbouring reference channel section 10 defines the second ARROW reflector whose refractive index corresponds essentially to that of the core 24, etc..

The arrangement of the planar channels shown in FIG. 3 permits thus ARROW waveguiding in the horizontal direction, whereas Bragg reflecting waveguiding is effected in the vertical direction.

For an optimization of the waveguiding, it is regarded as a preferred embodiment when the thickness $d_{R2}$ of the respective even-numbered ARROW reflectors, which are arranged in pairs and which are defined by the reference channel sections 8, 9, 10, 11, is an odd multiple of half the thickness of the core $d_c$, although this is not decisive with respect to the mode of operation of the Bragg waveguiding according to the present invention, said Bragg waveguiding being effected within the optical detector device in the direction of the propagation of light from the light entry boundary surface 25. The thickness $d_{R2}$ of these resonator layers generally satisfies the following equation:

$$d_{R2} \approx (2i-1)d_c/2, i = 1,3,5$$

Considering only a single vacuum wavelength $\lambda$ of the light travelling along the light path, the optimum thickness of the odd-numbered resonator layers $d_{R1}$, which is defined by the material of the detector body between the core 24 and the reference channel section 10, is given by the following equation:

$$d_{R1} \approx \frac{\lambda}{4n_1}\left[1-\left(\frac{n_c}{n_1}\right)^2 + \left(\frac{\lambda}{2n_c d_c}\right)^2\right]^{-1/2}(2i-1),$$
$$i = 1,3,5 \ldots$$

In the above equation $n_c$ is the refractive index of the core 24, whereas $n_1$ is the refractive index of the first layer and, consequently, of the material of the detector body 12.

This equation holds only for a spectral range of some ten nm. For a broadband transmission, the thickness $d_{R1}$ can be chosen to an arbitrary thickness.

Figure 4:
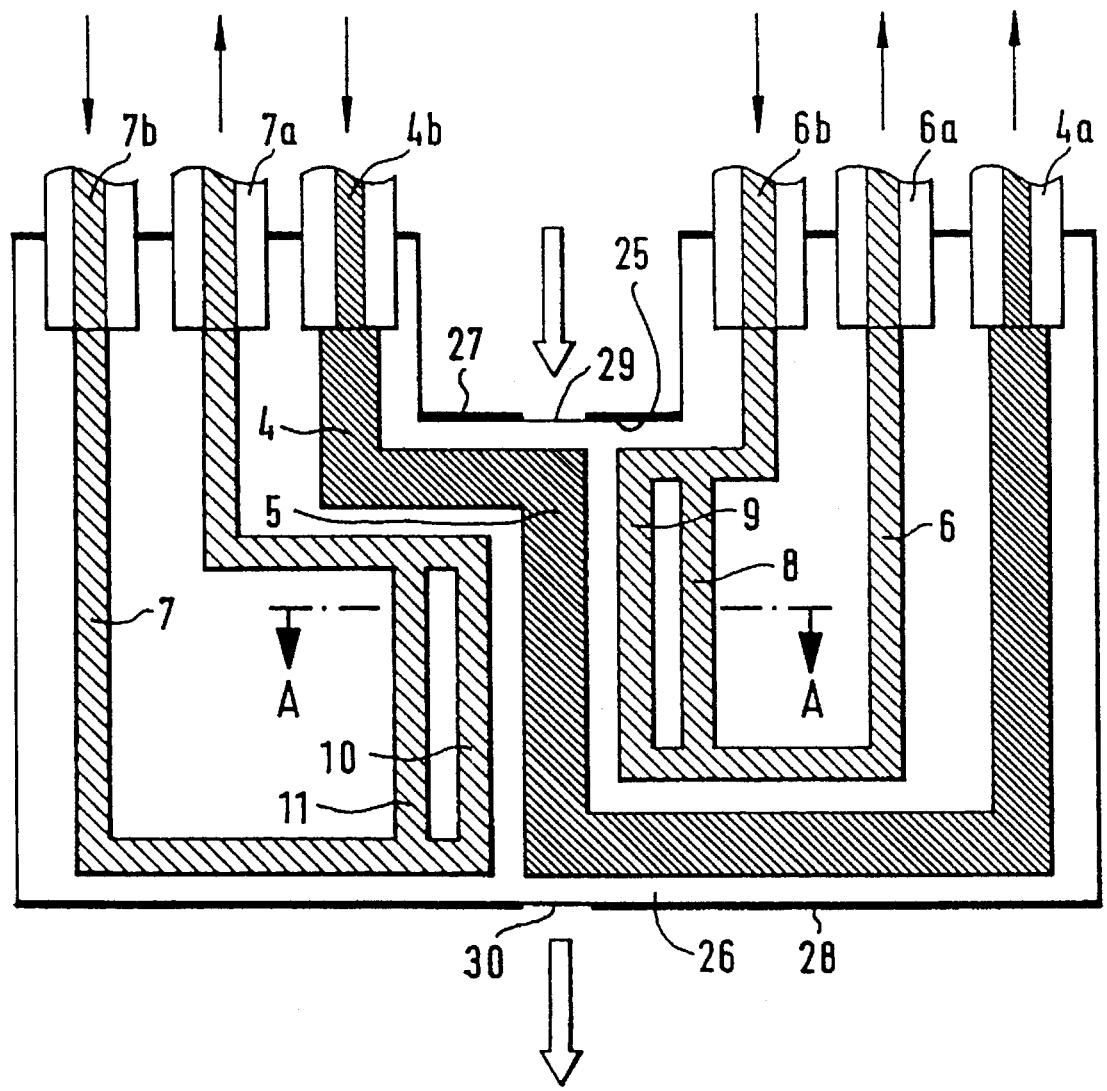
FIG. 4 shows a slightly modified embodiment in a representation corresponding to FIG. 2, comprising optical slits.

The slightly modified embodiment, a sketch of which is shown in FIG. 4, differs from the embodiment described with reference to FIG. 1 to 3 only insofar as the light path between the light entry boundary surface 25 and the light exit boundary surface 26 is limited by mirrored or blackened regions 27, 28, which are used for defining window areas 29, 30 and the lateral dimensions of which correspond essentially to the width of the analyte channel 4, said mirrored or blackened regions being applied to said boundary surfaces.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. An optical detector device for analytical measurement systems, in particular for use in liquid chromatography systems or capillary electrophoresis systems, comprising:

an analyte channel through which a fluid containing the analyte can be guided, and a light path extending through said analyte channel into which light coming from a light source can be introduced and from which light can be coupled out and introduced in an optoelectric sensor element of the analytical measurement system, at least part of the light path being defined by a waveguide, which is constructed at least partially as a Bragg waveguide structure in such a way that the light is guided through the analyte channel essentially in the channel direction at least along a sublength of said analyte channel, said Bragg waveguide structure exhibiting Bragg reflecting layers in a plane extending through the analyte channel, and further defined by an antiresonant reflecting waveguide structure in an additional plane which is perpendicular to said first-mentioned plane and which also extends through said analyte channel.

2. An optical detector device according to claim 1, comprising reference channels acting as reflectors only, wherein the refractive index of a substance within these reference channels is similar to that of the fluid in the analyte channel.

3. An optical detector device according to claim 1, wherein the analyte channel extends through an optically transparent detector body, at least one reference channel extending on either side of the analyte channel in parallel, spaced relationship therewith so that the analyte channel and the reference channels define in said detector body an antiresonant reflecting optical waveguide structure which is effective in a first plane.

4. An optical detector device according to claim 3, wherein the analyte channel is provided with Bragg reflecting layers on two opposed boundary layers, said Bragg reflecting layers defining a Bragg waveguide structure in a second plane which extends perpendicular to the first plane.

5. An optical detector device according to claim 3, wherein the detector body comprises a substrate member and a cover member, said analyte channel and said reference channels being etched into said substrate member and/or said cover member with an essentially rectangular cross-section.

6. An optical detector device according to claim 1, wherein said Bragg waveguide structure employs Bragg waveguiding in both vertical and horizontal directions.

7. An optical detector device according to claim 5, wherein the size of the cross-sectional dimensions of the analyte channel and of the reference channels is between 1 micrometers and 100 micrometers.

8. An optical detector device according to claim 1, wherein a core of the waveguide is defined by the analyte channel.

9. An optical detector device according to claim 2, constructed in an optically transparent detector body, wherein a refractive index of the optically transparent detector body is higher than the refractive index of the fluid in the analyte channel and is also higher than the refractive index of the fluid in the reference channels so that areas of the detector body which are located between the analyte channel and the reference channels positioned adjacent said analyte channel act as first ARROW reflectors, whereas said reference channels positioned adjacent the analyte channel act as second ARROW reflectors, and areas which are located between the respective reference channels act as additional ARROW reflectors.

* * * * *